United States Patent [19]

Marin et al.

[11] 4,171,323

[45] Oct. 16, 1979

[54] SURFACE-ACTIVE AGENT

[75] Inventors: Pierre D. Marin, Rouen; Marcel Prillieux; Robert Tirtiaux, both of Mont-Saint-Aignan, all of France

[73] Assignee: Exxon Research & Engineering Co., Florham Park, N.J.

[21] Appl. No.: 845,565

[22] Filed: Oct. 26, 1977

Related U.S. Application Data

[63] Continuation of Ser. No. 648,120, Jan. 9, 1976, abandoned.

[30] Foreign Application Priority Data

Jan. 17, 1975 [GB] United Kingdom ............... 2123/75

[51] Int. Cl.$^2$ ........................................... C07C 143/26
[52] U.S. Cl. ......................... 260/501.19; 252/8.55 D
[58] Field of Search ...................................... 260/501.19

[56] References Cited

U.S. PATENT DOCUMENTS

| | | | |
|---|---|---|---|
| 2,778,814 | 1/1957 | Behrens et al. ................. | 26/98 |
| 3,861,466 | 1/1975 | Gale ................................ | 260/501.19 |
| 3,983,940 | 10/1975 | Carpenter, Jr. et al. ........ | 260/501.19 |

FOREIGN PATENT DOCUMENTS 1391916  4/1975  United Kingdom ............... 260/501.19

*Primary Examiner*—Bernard Helfin
*Assistant Examiner*—G. T. Breitenstein
*Attorney, Agent, or Firm*—Frank T. Johmann

[57] ABSTRACT

Surface active agents for oil in water emulsions and oil recovery comprising salts of alkaryl sulphonic acids and organic bases containing at least one —$(C_2H_4O)_nH$ where n is greater than 1.

10 Claims, No Drawings

SURFACE-ACTIVE AGENT

This is a continuation of application Ser. No. 648,120, filed Jan. 9, 1976, now abandoned.

This invention is concerned with a surface-active agent and with some of its applications, in particular to the use of this surface-active agent in emulsifiable lubricants and in the working of oil deposits.

The main aim of the invention concerns a new type of surface-active agent different variants of which, adapted to special uses, can be made.

Emulsifiable lubricating compositions are used regularly in certain industries. For instance, for machining metals, the tool is lubricated and cooled by sprinkling it with a liquid which, in most cases, is an emulsion consisting of a special lubricant, termed "cutting oil", dispersed in water.

Alkaryl sulphonates are among the most used emulsifiers, not only in emulsifiable lubricating compositions, but also in the most varied emulsions. Nevertheless, the emulsifying power of many of the present known alkaryl sulphonate, is insufficient to obtain stable aqueous emulsions and there must be added to the usual alkaryl sulphonates one or more emulsifiers of another type, for instance salts of fatty acids or nonionic surface-active agents. One reason for the instability of emulsions using many of the known alkaryl sulphonates is the presence of mineral ions which tends to break up the emulsion.

One of the embodiments of the invention furnishes salts which act as emulsifiers with which it is possible to obtain stable aqueous emulsions, without it being necessary to add to it a surface-active agent belonging to another class.

Another embodiment of the invention is concerned with the need for surface-active agents endowed with special properties in the oil production industry. The working of a deposit by the conventional means, such as natural gushing, pumping and the injection of gas or water under pressure, makes it possible to extract only the petroleum that is able to flow freely through the gaps in the storage rock. When the conventional means become inoperative, the deposit also contains considerable quantities of crude which the rock retains by capillary absorption. Consideration has for long been given to extracting the petroleum thus added by displacing it with water, with the addition of a suitable surface-active agent. The latter, in very low concentration in water must lower the interfacial pressure between the water and the hydrocarbons to 1 dyne/cm or even less. Although a number of surface-active agents have been proposed they have not been sufficiently insensitive to sodium chloride, which is present in every oil deposit, to allow the defined emulsion to be formed. U.K. Pat. No. 1,391,916 suggests a surface-active agent comprising a salt of certain alkaryl sulphonic acids and organic bases and this is superior in this respect to similar earlier products. A surface active agent that is still more insensitive to sodium chloride than that described in this patent would definitely be of interest.

One of the embodiments of this invention provides a surface-active agent which is quite compatible with sodium chloride and makes it possible to lower the interfacial tension between the water and the hydrocarbons to 1 dyne/cm or even less.

According to this invention a surface-active agent comprises a salt of an alkarylsulphonic acid the mean molecular weight of which is between 250 and 1,000, and an organic base the molecules of which include at least one—$(C_2H_4O)_n$—H group, n denoting a number larger than 1 and smaller than 40.

U.K. Pat. No. 1,391,916 suggests that the organic base may be mono-, di- or tri ethanolamine but we find that the presence of additional—$(C_2H_4O)$—groups in the compounds of the present invention leads to improved brine compatibility. Surfactant Systems containing—$(C_2H_4O)n$ groups have been proposed as detergents in, for example, British Pat. No. 1,296,351 and German Pat. No. 1,088,173 but these suffer from the disadvantage for the purposes envisaged that since they are derived from sodium sulphonates and quaternary ammonium halides they generate mineral ions which would impair their compatibility with brine and render them unsuitable in oil recovery.

The mean molecular weight of the alkaryl sulphonic acids is between 250 and 1,000 and can vary according to the particular use for which the surface-active agent is intended. The optimum mean molecular weight is in most cases between 300 and 600. These acids can be of the type of those obtained by sulphonating a suitable fraction of crude petroleum. These are for preference alkylbenzene sulphonic acids obtained by sulphonation of synthetic alkylbenzenes. It is possible to prepare alkylbenzenes that are suitable for carrying out the invention by alkylating an aryl hydrocarbon the molecule of which contains from 6 to 10 carbon atoms, such as benzene, toluene, ethylbenzenes, with olefins or chloroparaffins having the appropriate mean molecular weight. The aryl hydrocarbon can be alkylated with an oligomer of a low molecular weight olefin. For preference, benzene, toluene or orthoxylene are alkylated with propylene oligomers having from 9 to 35 carbon atoms per molecule.

It is possible to sulphonate alkylaromatic hydrocarbons by any appropriate means. A good process for sulphonating alkylbenzenes comprises using sulphur trioxide in solution in liquid sulphur dioxide at a temperature of less than $-5°$ C.

The organic base from which the surface-active agent is derived is obtained by a reaction consisting of the poly-addition of ethylene oxide to ammonia or to an organic compound the molecule of which includes at least one basic functio and at least one mobile hydrogen atom. The basic organic compounds that can be used, include in particular primary or secondary amines, polyamines and alkanolamines and are preferably ethoxylated alkylamines or polyamines containing either a primary or secondary amine function. Example of suitable basic compounds are triisopropanolamine and better still triethanolamine. The average number of mols of ethylene oxide attached to each mol of the basic compound is selected as a function of the nature of the latter and as a function of the particular use for which the surface-active agent is intended. We prefer that were the organic base contains alkyl groups they be short chain (i.e. less than 6 carbon atoms) as long chains can lower compatibility with water.

A first variant of the surface-active agent according to the invention is particularly suitable for emulsifying a hydrocarbon phase in an aqueous phase. In this variant, the mean molecular weight of the alkarylsulphonic acids is between 400 and 1000, and for preference between 400 and 600, e.g. 450 to 600. The base is obtained for preference by condensing ethylene oxide on an alkanolamine such as, triisopropanolamine or better still on triethanolamine. The optimum means molecular weight of the acids, and the optimum molar ratio between ethylene oxide and alkanolamine depend on the particular nature of the two phases to be emulsified.

For preference, the acids are obtained by sulphonation of alkylbenzenes derived from alkylation of benzene by a propylene oligomer. By distilling the benzene alkylation product with tetrapropylene, the dodecyl benzene is separated, as well as a heavy residue consisting mainly of dialkyl benzenes. It is possible to use the acids obtained by sulphonating this distillation residue. For preference, acids are used which are obtained by sulphonating the product of alkylation of benzene by an oligomer the mean molecular weight of which is between 250 and 450.

More especially, the salt of alkylbenzene sulphonic acids the mean molecular weight of which is between 450 and 550, and the product obtained by condensing 1 to 4 mols of ethylene oxide on 1 mol triethanolamine is exceptionally efficacious for dispersing a mineral lubricating oil. The optimum molar ratio between ethylene oxide and triethanolamine is between 1 and 4 according to the nature of the hydrocarbon oil, as will be seen from one of the examples given at the end of the present specification.

A second variant of the surface-active agent according to the invention combines a powerful lowering of the interfacial tension between water and hydrocarbons. With an improved compatibility compared with previous similar products. This variant is therefore especially suitable for extracting oil from a deposit through displacing with water. In this variant the mean molecular weight of the alkarylsulphonic acids is between 250 and 400, for preference between 300 and 400. These acids can be obtained by sulphonation of an appropriate crude oil fraction. They are obtained for preference by the sulphonation of alkybenzenes derived from the alkylation of orthoxylene. The orthoxylene is for preference alkylated with tetrapropylene. For preference, the base is the product that is obtained by condensing at least 1 mol of ethylene oxide on 1 mol of triethanolamine.

The higher the proportion of ethylene oxide, the better the compatibility of the surface-active agent with sodium chloride. The lowering of the interfacial tension remains excellent whatever the proportion of ethylene oxide contained in the base. These results were in no way foreseeable.

It is difficult to add more than 20 mols of ethylene oxide to 1 mol of triethanolamine. In practice, highly satisfactory results are obtained by condensing from 2 to 10 mols of ethylene oxide per mol of triethanolamine.

The invention does not only relate to the surface-active agent just described. It also relates to an emulsifiable lubricating composition characterised in that it contains from 1 to 50% of its weight of a suitable surface-active agent of this type, the balance consisting of a base oil and additives selected as a function of the special use for which the composition is intended.

A particular form of this composition is a cutting oil for metal working, based on mineral oil the viscosity of which is between 5 and 100 cSt at 40° C. This cutting oil contains from 1 to 5% by weight of one or more extreme pressure lubricating agents, from 1 to 5% by weight of one or more bactericidal agents and 1 to 5% by weight of anti-corrosion agents. In accordance with the invention it contains as emulsifier from 10 to 50% by weight of the appropriate surface-active agent of the type described above.

The invention finally relates to a process for improving the extraction of oil from an underground deposit. This process comprises the injection into the deposit of a solution (e.g. an aqueous solution) containing the appropriate surface-active agent of the type described above, the displacement of the oil with this solution in the oil-bearing rock and the extraction of the oil thus displaced.

For preference, the acids contained in the surface-active agent are dodecylxylene sulphonic acids and the base is the product obtained by condensing 1 to 20, or for preference 3 to 10 mols of ethylene oxide on 1 mol of triethanolamine.

According to a variant of this process, the solution containing the surface-active agent is injected into one well and the displaced oil is extracted by another well.

The present invention is illustrated but in no way limited by reference to the following Examples:

EXAMPLE 1

This example relates to the emulsification of mineral oils.

It was proposed to emulsify three tyical mineral oils which differed in their respective contents of aromatic carbon atoms, naphthenic and paraffinic carbon atoms (table I below).

Alkylbenzene sulphonic acids were prepared having a mean molecular weight of 500 by sulphonating monalkylbenzenes at −10° C. with sulphur trioxide dissolved in liquid sulphur dioxide. The monoalkylbenzenes were prepared by alkylation of benzene with a propylene oligomer, the mean molecular weight of which was 340.

Ethylene oxide was injected into triethanolamine kept at 100° C., so as to obtain a series of addition products in which were condensed 1 to 6 mols of ethylene oxide per mol of triethanolamine.

Each of these additional products was finally neutralised with the previously prepared acids, and the emulsifying power of the surface-active agents thus obtained was compared.

Each test was carried out accordingly to the following method of operation. 1 part by weight of the product being tested was mixed with 4 parts by weight of oil. 5 parts by weight of this composition were dispersed in 95 parts by weight of water whose hydrotimetric titre was 22°. An emulsion was obtained which was allowed to stand at 20° C. in a graduated stoppered test tube. After standing for 24 hours there was read off on the graduation of the test tube the volume of the cream or of the separated oil. The result was expressed as % of the total volume.

The results thus obtained are collated in Table II below. It will be seen that the emulsifier according to the invention makes it possible to disperse in water any type of mineral oil, even a higher paraffinic oil. It is nevertheless well known that paraffinic oils are difficult to emulsify.

TABLE I

| CHARACTERISTICS OF OILS TO BE EMULSIFIED | | | |
|---|---|---|---|
| Referenc | A | B | C |
| Oil type | Naphthenic | Paraffinic | Very Paraffinic |
| Viscosity at 99° C. (cSt) | 3.6 | 3.9 | 5.5 |
| Atoms of aroatic carbon (%) | 21 | 20 | 7 |
| Atoms of naphthenic carbon (%) | 25 | 23 | 24 |
| Atoms of paraffinic | 54 | 57 | 69 |

TABLE I-continued

| CHARACTERISTICS OF OILS TO BE EMULSIFIED | | | |
|---|---|---|---|
| Referenc | A | B | C |
| carbon (%) (by I.R. spectrophotometry) | | | |

TABLE II

SEPARATION OF EMULSIONS AS A FUNCTION OF PROPORTION OF ETHYLENE OXIDE ADDED TO TRIETHANOLAMINE

| Moles EO | Oil Reference | | |
|---|---|---|---|
| Mole tea | A | B | C |
| 0 | 10.0 | 6.0 | 7.0 |
| 1 | 0.5 | 4.5 | 5.5 |
| 2 | 2.0 | 2.75 | 4.0 |
| 3 | 3.0 | 0.75 | 1.75 |
| 4 | 3.5 | 1.0 | 3.5 |
| 5 | 4.5 | 3.0 | 4.75 |
| 6 | 4.75 | 5.0 | 5.75 |

EXAMPLE 2

This example relates to a surface-active agent according to the invention and intended for use to lower the interfacial tension between brine and hydrocarbons, in the working of oil deposits.

Orthoxylene was alkylated with tetrapropylene and the alkylate obtained was sulphonated. The dodecylorthoxylene sulphonic acids thus prepared has a mean molecular weight of 360.

A series of surface-active agents according to the invention was prepared by neutralising these acids with triethanolamine to which had been added varying proportions of ethylene oxide as in Example 1.

By way of comparison, surface-active agents of known type were prepared by neutralising the same acids with sodium hydroxide, monoethanolamine, diethanolamine and triethanolamine. It is known that the dodecylorthoxylene sulphonates of alkanolamines are reputed to have good compatibility with sodium chloride.

To evaluate the compatibility of the surface-active agents with brine, the following test was conducted.

The surface-active agent was dissolved in water and in a concentration of 1% by weight. The solution was divided into a certain number of portions in which sodium chloride in different concentrations was dissolved. Each solution was allowed to stand at 20° C. in a graduated test-tube. After standing for 24 hours, the samples were inspected and the sodium chloride concentration was noted below which the volume of the deposits and creaming was less than 1% of the total volume.

The results obtained are shown in Table III below. It will be seen that the invention indeed makes it possible to obtain surface-active agents whose compatibility with sodium chloride is very much better than that of the best former similar products.

Finally, the interfacial tension was measured between benzene and aqueous solutions which each contained one of the emulsifiers and 1% sodium chloride. Each emulsifier was tested in different concentrations. The results are collated in Table IV below.

It will be seen that efficacy of the surface-active agents according to the invention is equal to that of the best product known.

TABLE III

| COMPATIBILITY OF SODIUM CHLORIDE | |
|---|---|
| Nature of base combined with sulphonic acids | Maximum NaCl concentration |
| Caustic Soda | 1.7 |
| MEA | 1.5 |
| DEA | 2.0 |
| TEA | 2.3 |
| TEA + 1.7 mole EO | 3.2 |
| TEA + 4.7 moles EO | 3.7 |
| TEA + 7.2 moles EO | 4.0 |
| TEA + 9.6 moles EO | 4.3 |

TABLE IV

| Interfacial Tension Between Benzene And Brine (Dynes/Cm) | | | |
|---|---|---|---|
| | Surfactant Concentration | | |
| Nature of Base | 0.01 | 0.1 | 1 |
| MEA | 1 | 0.4 | 0.3 |
| DEA | 1 | 0.4 | 0.3 |
| TEA | 1 | 0.4 | 0.3 |
| TEA + 1.7 mole EO | 1 | 0.4 | 0.3 |
| TEA + 4.7 moles EO | 1 | 0.4 | 0.3 |
| TEA + 7.2 moles EO | 1 | 0.4 | 0.3 |
| TEA + 9.6 moles EO | 1 | 0.4 | 0.3 |

EXAMPLE 3

Surfactive agents of the present invention were prepared under the same conditions as in Example 1 employing the same sulphonate but using ethoxylated dimethylamine instead of ethoxylated triethanolamine and oil A. The emulsions were tested as in Example 1 and the phase separation after 24 hours was as follows:

| Moles Ethylene Oxide per mole of $(CH_3)_2NH$ | Phase Separation After 24 Hours (Vol %) |
|---|---|
| 1 | 5 |
| 2 | 4.5 |
| 3 | 4 |
| 4 | 1 |
| 5 | 2.5 |
| 6 | 4 |
| 7 | 4.5 |
| 8 | 5 |

We claim:

1. A salt, which is a surface active agent for oil in water emulsions and having improved sodium chloride brine compatibility, of an alkarylsulphonic acid the mean molecular weight of which is between 250 and 1000 and an organic base, said organic base being the addition product of one to 10 moles of ethylene oxide per mole of trialkanolamine having alkyl groups of less than six carbon atoms.

2. A salt according to claim 1, in which the mean molecular weight of the alkarylsulphonic acid is between 300 and 600.

3. A salt according to claim 1, in which the mean molecular weight of the alkarylsulphonic acid is between 450 and 600.

4. A salt according to claim 2, in which the base is obtained by condensing about 1 to 6 moles of ethylene oxide on trialkanolamine.

5. A salt according to claim 4, in which the alkanolamine is triethanolamine.

6. A salt according to claim 4, in which from 1 to 4 moles of ethylene oxide are condensed onto 1 mole of the trialkanolamine.

7. A salt according to claim 1, in which the alkaryl sulphonic acid is an alkylbenzene sulphonic acid of mean molecular weight between 450 and 550 and the base is obtained by condensing from 1 to 4 moles of ethylene oxide on 1 mole of triethanolamine.

8. A salt according to claim 1, in which the mean molecular weight of the alkaryl sulphonic acid is between 250 and 400.

9. A salt according to claim 8, in which the alkaryl sulphonic acid is derived from the alkylation of orthoxylene.

10. A salt according to claim 9, in which the orthoxylene is alkylated with tetrapropylene.

* * * * *